United States Patent [19]

Trought

[11] 4,173,281
[45] Nov. 6, 1979

[54] INTRAOCULAR LENS PACKAGING SYSTEM

[75] Inventor: John H. Trought, Richwood, Tex.

[73] Assignee: Intermedics Intraocular, Inc., Freeport, Tex.

[21] Appl. No.: 914,800

[22] Filed: Jun. 12, 1978

[51] Int. Cl.² ............... B65D 81/18; A61F 1/16; A61F 1/18; B65D 25/54

[52] U.S. Cl. ............... 206/5.1; 206/45.34; 206/210; 206/439; 356/246

[58] Field of Search ............... 206/5.1, 210, 0.8, 45.34, 206/365, 439; 356/246

[56] References Cited

U.S. PATENT DOCUMENTS

| | | | |
|---|---|---|---|
| 2,998,126 | 8/1961 | Jenkins | 206/45.34 |
| 3,155,236 | 11/1964 | Reno | 206/45.34 |
| 3,485,239 | 12/1969 | Vanderbeck | 206/365 |
| 3,837,475 | 9/1974 | Bolanz | 206/0.8 |
| 4,113,088 | 9/1978 | Binkhorst | 206/210 |

Primary Examiner—William T. Dixson, Jr.

[57] ABSTRACT

An optically clear sterile intraocular lens packaging system which allows inspection and measurement of the lens without breaking sterility. The packaging system includes an outer case, an inner case within the outer case, and means for mounting the lens within the inner case. The inner and outer cases both have tops and bottoms, wherein at least a portion of the tops and bottoms have optically flat transparent surfaces parallel to each other. The mounting means is adapted to mount the lens in a plane parallel to the transparent surfaces of the inner and outer cases.

13 Claims, 6 Drawing Figures

INTRAOCULAR LENS PACKAGING SYSTEM

BACKGROUND OF THE INVENTION a. Field of the Invention

The present invention relates generally to an intraocular lens packaging system, and more particularly to an optically clear sterile intraocular lens packaging system which allows inspection and measurement of the lens without breaking sterility.

b. Description of the Prior Art

In the healthy eye, light is focused on the retina by a natural crystalline lens. In certain individuals, the crystalline lens becomes cloudy and opaque, which results in the condition known as a cataract and which results in a loss of vision. One method of treating cataracts is the surgical removal of the natural crystalline lens, thereby allowing light to again be received by the retina. However, without the crystalline lens, the light that reaches the retina is unfocused and therefore, normal vision still is impossible. Normal vision is restored by means of artificial lenses, which may be in the form of eyeglasses, contact lenses worn over the cornea or intraocular lenses implanted within the eye itself.

Intraocular lenses come in a variety of styles and ranges of powers. The style of lens is dictated primarily by the preference of the surgeon for any of various surgical procedures for implanting the lens. The power of the lens is dictated by the size and shape of the individual eye and whether the lens is fixed anterior or posterior to the iris.

Presently, intraocular lenses are packaged either in dry sterile envelopes with opaque lens cases or sterile transparent tubes with a liquid therein. Information as to the power and style of the lens is normally printed on a label affixed to the package. However, prudent surgical practice requires that the surgeon or one of his associates inspect the lens to verify that the labeling information is correct. The inspection is normally performed under sterile conditions in the operating room immediately prior to implantation of the lens and involves removing the lens from the package, visually inspecting the lens for style and defects, and measuring the power of the lens with a device known as a lensometer. If it develops that the lens is defective, the lens is normally discarded rather than being repackaged and relabeled, which is a costly and wasteful procedure.

A further shortcoming of the prior intraocular lens packaging systems lies in maintaining sterility. The lens packaging material is brought into the operating room from the outside and therefore the outside thereof is unsterile. The prior systems provide no means for assuring sterility of the lens after the systems are opened.

SUMMARY OF THE INVENTION

It is therefore the object of the present invention to provide an intraocular lens packaging system that overcomes the shortcomings of the prior systems. It is a principal object of the present invention to provide a packaging system by which inspection and measurement of the lens may be made in an unsterile environment without breaking the sterility of the lens. It is a further object of the present invention to provide a packaging system that minimizes the possibility of breaking the sterility of the lens during transition from the outside environment to the sterile operating room environment.

Briefly stated, the foregoing and other objects of the present invention are accomplished by providing an optically clear sterile intraocular lens packaging system which allows inspection of the lens without breaking sterility. The lens packaging system includes an outer case having a top and a bottom. At least a portion of the top and bottom of the outer case have optically flat transparent surfaces that are parallel to each other.

Within the outer case is an inner case also having a top and a bottom. At least a portion of the top and bottom of the inner case have optically flat transparent surfaces parallel to each other and parallel to the optically flat transparent surfaces of the other case. Means are provided for mounting the lens within the inner case such that the lens lies in a plane parallel to the transparent surfaces of the inner and outer cases. The lens therefore may be inspected from the top to determine the style thereof while the lens is within the packaging system. Additionally, the system can be inserted into a lensometer. Since the optical surfaces of the system are optically flat and transparent and parallel to each other, and parallel to the plane of the lens, the power of the lens can be measured without any refraction from the optical surfaces of the packaging system. Additionally, the resolution of the optical surfaces of the packaging system is greater than that of the lens, thereby making gross inspection of the resolution of the lens possible. Additionally, means are provided for viewing the sides of the lens from the outside of the packaging system thereby allowing complete visual inspection of the lens.

Means are provided for introducing a sterilizing agent into the packaging system and maintaining the inside thereof sterile while the outisde is unsterile. The construction of the packaging system of the present invention allows the system to be brought from the outside into the operating room and opened by a circulating nurse without breaking the sterility of the inner case. If the inner case does inadvertently become contaminated, the construction allows the lens to be removed in a sterile condition.

DESCRIPTION OF THE PREFERRED EMBODIMENT

Figure 1:
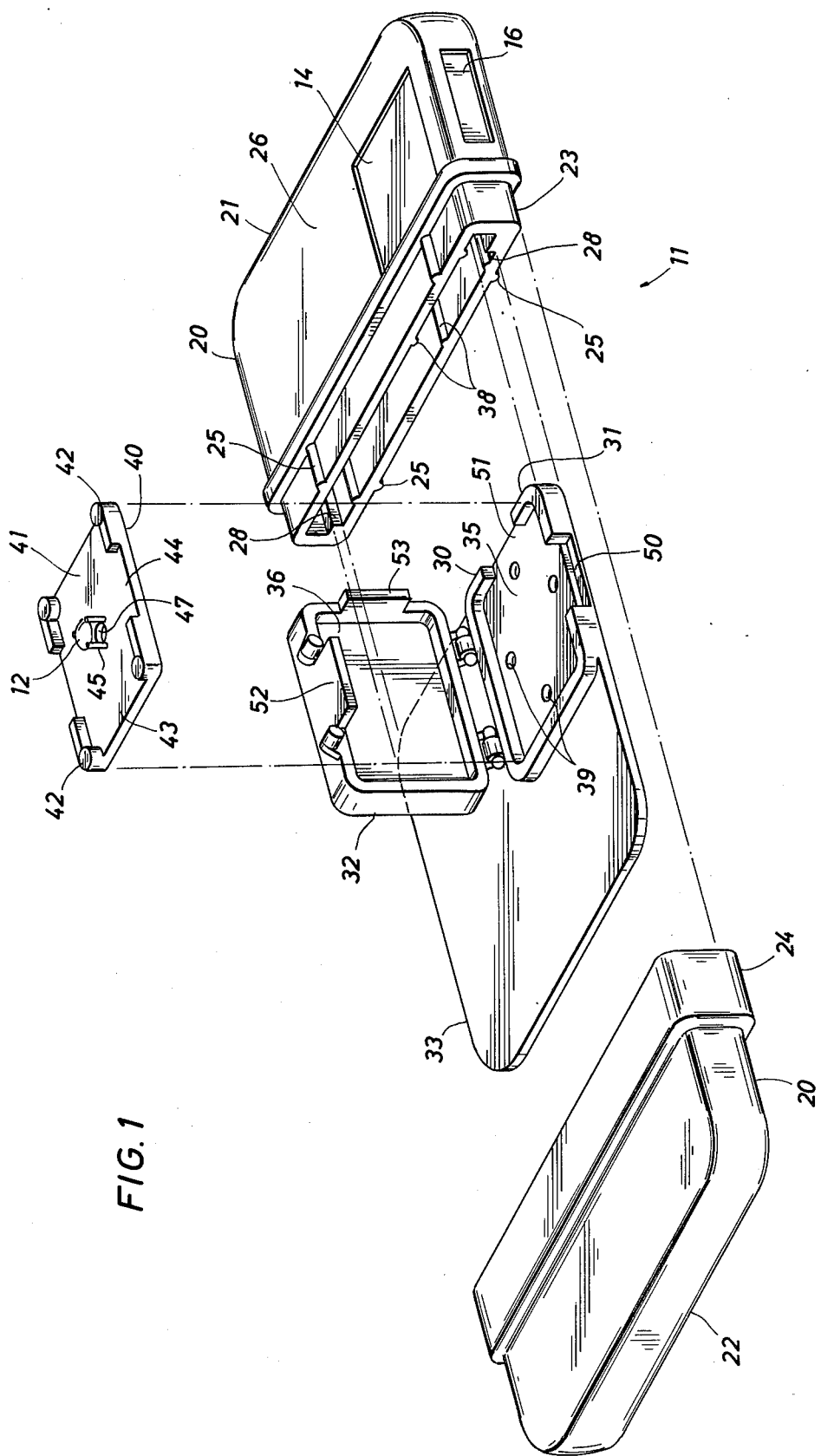
FIG. 1 is an exploded perspective view of the preferred embodiment of the lens packaging system of the present invention.

Referring now to the drawings, the packaging system of the present invention is designated generally by the numeral 11 and is adapted to provide an optically clear sterile package for an intraocular lens, designated by the numeral 12, that allows inspection of lens 12 without breaking sterility. Packaging system 11 is comprised of an outer case 20, an inner case 30, and means for mounting lens 12 within inner case 30, which in the preferred embodiment includes a mounting tray 40.

Outer case 20 includes a viewing portion 21 and a cap portion 22. In the preferred embodiment, viewing portion 21 and cap portion 22 are hollow shells of clear plastic which when joined together form outer case 20. Viewing portion 21 and cap portion 22 are joined together by inserting a plug 23 at the open end of viewing portion 21 into a socket 24 at the open end of cap portion 22. A plurality of spacer ribs 25 are provided on plug 23 to space the outside of plug 23 apart from the inside of socket 24 to allow the flow of gas into and out of the inside of outer case 20, as will be detailed hereinafter.

Figure 3:
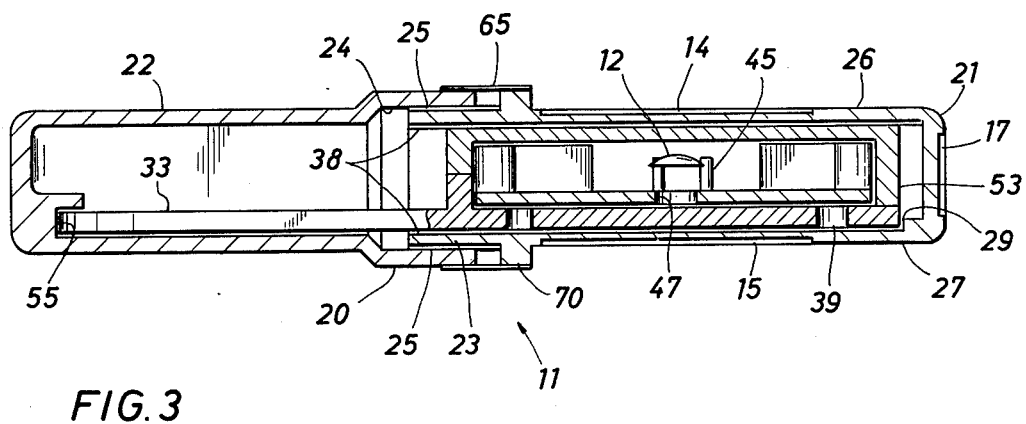
FIG. 3 is a sectional view along line 3—3 of FIG. 2.
Figure 4:
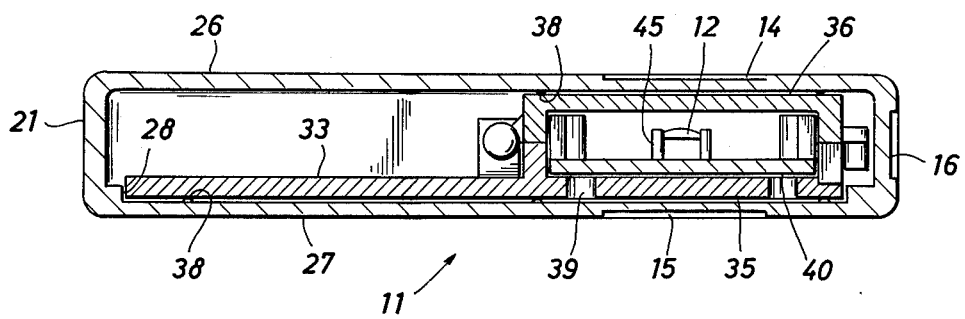
FIG. 4 is a sectional view taken generally along line 4—4 of FIG. 2.

Viewing portion 21 includes a top 26 and a bottom 27, as best shown in FIGS. 3 and 4. At least a portion of top 26 and bottom 27 includes an optically flat surface, which in the preferred embodiment form top window 14 and bottom window 15. Windows 14 and 15 are parallel to each other and overlie each other such that light rays perpendicular to the planes of windows 14 and 15 may pass therethrough without being refracted. Windows 14 and 15 are recessed within top 26 and bottom 27 to prevent their being scratched.

In order to allow further viewing of the inside of outer case 20, a side window 16 and an end window 17 are provided in viewing portion 21 of outer case 20. Windows 16 and 17 are recessed in similar fashion to windows 14 and 15 and are positioned to allow viewing into the space between windows 14 and 15.

Inner case 30 is formed of clear plastic and is comprised generally of a bottom 31 hingedly connected to a top 32. Bottom 31 has integrally formed therewith a generally square laterally extending flange 33, which serves to position inner case 30 properly within outer case 20 and provides means by which inner case 30 may be inserted into and removed from viewing portion 21. Flange 33 also provides space upon which labels and the like may be applied.

Figure 2:
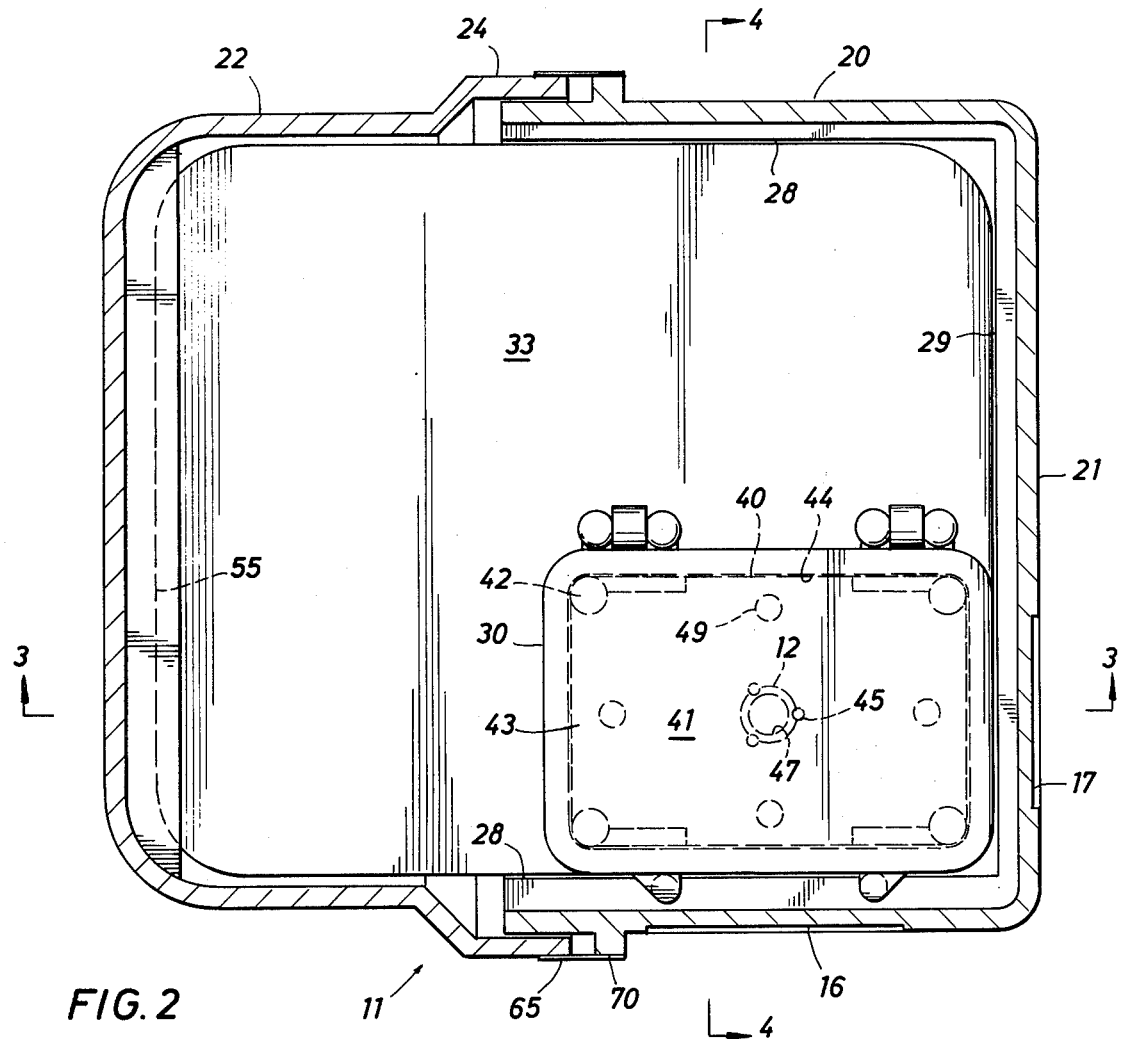
FIG. 2 is a top partial sectional view of the lens packaging system of the present invention in the assembled condition.

The lower portion of bottom 31 of inner case 30 forms an optically flat lower window 35 and the upper portion of the top 32 of inner case 30 forms an optically flat upper window 36. When inner case 30 is closed, as shown in FIGS. 2-4, lower window 35 and upper window 36 are parallel to each other. A plurality of ribs 38 are provided in the interior of viewing portion 21 of outer case 20 in order to align lower window 35 and upper window 36 of inner case 30 parallel to top window 14 and bottom window 15 of outer case 20, such that light rays may pass through windows 14, 15, 35 and 36, perpendicular to the planes thereof without being refracted. Ribs 38 also serve to space apart windows 35 and 36 of inner case 30 from windows 14 and 15 of outer case 20 to prevent scratching thereof and to allow the flow of gas around case 30 and into the interior thereof through a plurality of gas ports 39, as will be detailed hereinafter.

In order to allow clear viewing into the interior of inner case 30 from the sides, a side viewing gate 50 and an end viewing gate 51 are provided in bottom 31 of inner case 30. A side window 52 and an end window 53 are provided in top 32 of inner case 30, which when put together with side gate 50 and end gate 51 to allow clear viewing from the side and back when inner case 30 is closed. Windows 52 and 53 are positioned to coincide with windows 16 and 17 when inner case 30 is inserted into outer case 20.

Mounting tray 40 is preferably formed of a flexible plastic and is shaped and sized to fit loosely into inner case 30. Mounting tray 40 has a flat bottom 41 which overlies lower window 35 of inner case 30 and is parallel thereto. At the corners of mounting tray 40 are four spacer posts 42, which serve to keep bottom 41 and lens 12 mounted thereon from contacting upper window 36 when packaging system 11 is inverted. Mounting tray 40 has at each end an end viewing gate 43, and at each side a side viewing gate 44. Gates 43 and 44 are positioned to allow clear end and side views of lens 12 from the outside of packaging system 11 when the parts thereof are assembled.

Figure 5:
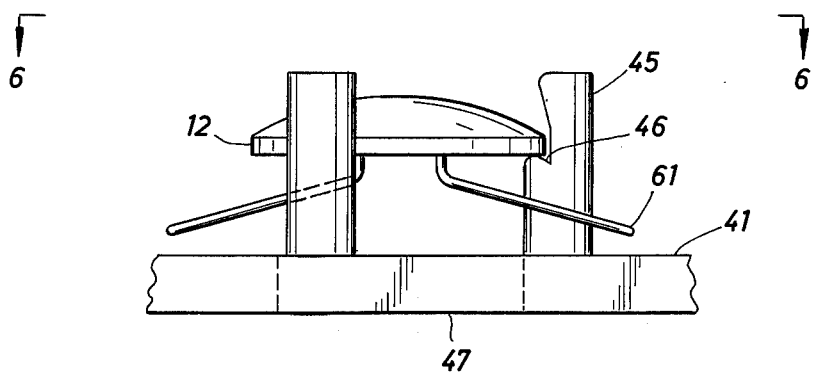
FIG. 5 is a fragmented view showing details of the lens mounting means.
Figure 6:
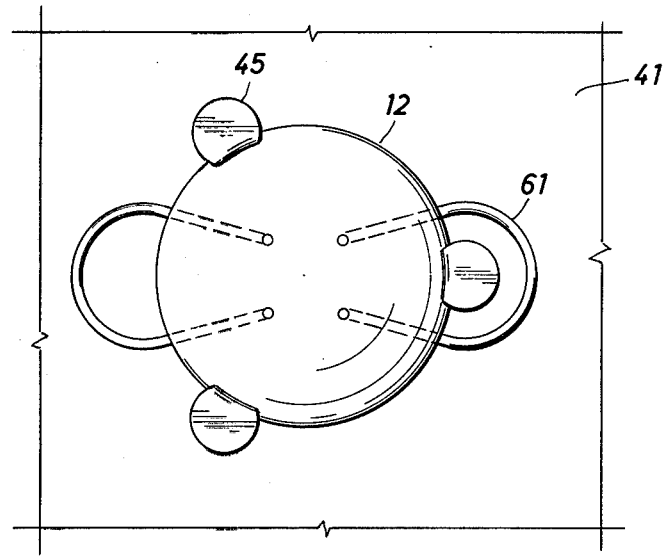
FIG. 6 is a top view taken along line 6—6 of FIG. 5 showing further details of the lens mounting means.

Lens 12 is mounted upon mounting tray 40 by means of at least a pair of mounting posts 45. Referring particularly to FIGS. 5 and 6, which depict the mounting of a lens 12 having two loops 61 and of the irido capsular style, wherein lens 12 is positioned anterior to the iris and loops 61 pass through the pupil and are fixed within the capsule vacated by the natural crystalline lens. Three mounting posts 45 are provided spaced circumferentially about lens 12 at approximately 120° intervals. It will of course be apparent to those skilled in the art that other configurations and spacing of mounting posts would be provided for mounting lens of different styles and that the configuration shown in the drawings is illustrative only.

Lens 12 is mounted to mounting posts 45 by means of notches 46. Notches 46 are positioned axially along mounting posts 45 equidistant from bottom 41 of mounting tray 40, such that lens 12 lies in a plane parallel to bottom 41.

Since mounting tray 40 is preferably of a soft flexible plastic, mounting tray 40 is usually translucent or opaque rather than transparent. Therefore, a circular viewing port 47 is positioned in bottom 41 immediately below lens 12 to allow viewing therethrough. To remove lens 12 from mounting posts 46, mounting tray 40 is simply inverted and finger-tip pressure is applied to the bottom thereof in the vicinity of port 47, whereupon posts 46 spread apart and lens 12 drops free of notches 46.

In operation, a lens 12 of a particular style and with a particular power is manufactured, and the style and power information is recorded on a label applied to flange 33. Lens 12 is inserted into notches 46 in mounting posts 45 and mounting tray 40 is deposited into bottom 31 of inner case 30, whereupon top 32 of inner case 30 is closed. Inner case 30 is then inserted into viewing portion 21 of outer case 20. Flange 30 engages a pair of side shoulders 28 and an end shoulder 29 whereby lens 12 is positioned for viewing through the various windows heretofore described.

With inner case 31 thus inserted into viewing portion 21, cap 22 is fitted over flange 33 such that socket 24 engages plug 23 as shown in FIGS. 2 and 3. A groove 55 is provided at the closed end of cap 22, which engages the end of flange 33 to keep the end of socket 24 from engaging the shoulder 70 adjacent to plug 23. Shoulder 70 is spaced apart from the end of socket 24 so as to allow the passage of gas into and out of packaging system 11.

After lens packaging system 11 has been assembled as aforesaid, a strip of microporous gas permeable tape is applied around the exterior of socket 24 and shoulder 70 thereby isolating the interior of packaging system 11 from the exterior thereof. The porosity of tape 65 is such that gas may pass therethrough but organisms may not.

After lens packaging system 11 has been sealed with tape 65, packaging system 11 is placed into a pressure vessel and a vacuum is drawn, which tends to purge the air from the interior of packaging system 11. Viewing port 47, gas ports 39, and ribs 25 and 38 allow free flow of gases within packaging system 11, thereby making system 11 completely purgeable.

After the air is evacuated from packaging system 11, the pressure chamber is pressurized with a sterilizing agent, for example, ethylene oxide gas. The ethylene oxide gas permeates tape 65 and floods the interior of packaging system 11. The ethylene oxide gas kills any organisms within packaging system 11 and thereby sterilizes lens 12.

After a time sufficient to insure destruction of all organisms, the pressure chamber is again evacuated, whereupon the ethylene oxide gas migrates back out of packaging system 11. After substantially all of the ethylene oxide gas has exited system 11, air is allowed to re-enter. Lens packaging system 11 may then be transported to the hospital for use.

At the hospital or in the surgeon's office, the surgeon or one of his associates can verify in an unsterile environment the correctness of the labeling information with respect to style and optical properties of lens 12. Lens 12 may be visually observed through top window 14, side window 16 and end window 17 to determine the style and quality thereof. Additionally, packaging system 11 can be inserted into a lensometer, which measures the focal length of lens 12. Windows 14, 15, 35 and 36, being optically flat and parallel to each other and to the plane of lens 12, do not refract the light passing through lens 12, whereby the lensometer measures only the power of lens 12. After the correctness of the labeling information has been verified, packaging system 11 may be stored for use.

At the time the surgeon desires to implant lens 12 into an eye, he prescribes the style and optical characteristics that are appropriate for the patient. A circulating nurse will then obtain the appropriate lens 12 within lens packaging system 11 from an unsterilized storage area and bring it into the sterilized operating room. Inside the operating room, the circulating nurse removes tape 65 and cap 22, thereby exposing sterilized flange 33. The circulating nurse presents flange 33 to a properly gloved and gowned scrub nurse who removes inner case 30 from viewing portion 21. The scrub nurse then removes mounting tray 40 from inner case 30 and delivers lens 12 to the surgeon for implantation.

If, during the removal of cap 22, the circulating nurse inadvertently touches flange 33, thereby contaminating flange 33 and the exterior of inner case 30, sterility of the interior of inner case 30 and lens 12 is maintained. The circulating nurse may carefully open top 32 of inner case 30 and invert inner case 30, allowing mounting tray 40, which is loosely fitted into inner case 30, to fall into the hands of the scrub nurse. The scrub nurse may then proceed to deliver lens 12 to the surgeon for implantation.

If the circulating nurse further inadvertently during opening the contaminated top 32 of inner case 30 touches mounting tray 40, sterility of lens 12 is still preserved. The circulating nurse may remove and invert mounting tray 40 and by the application of fingertip pressure in the vicinity of view port 47 allow lens 12 to drop into the hands of the scrub nurse, who may then deliver lens 12 to the surgeon for implantation.

It may therefore be seen that the present invention provides an optically clear sterile intraocular lens packaging system which allows complete inspection of the lens without breaking the sterility thereof. The invention further offers maximum safeguards to the sterility of the lens in the transition from an unsterile environment into the operating room.

Further modifications and alternative embodiments of the apparatus of this invention will be apparent to those skilled in the art in view of this description. Accordingly, this description is to be construed as illustrative only and is for the purpose of teaching those skilled in the art the manner of carrying out the invention. It is to be understood that the form of the invention herewith shown and described is to be taken as the presently preferred embodiment. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. An intraocular lens packaging system, which comprises:
    an outer case having a top and a bottom, wherein at least a portion of said top and bottom have optically flat transparent surfaces parallel to and substantially overlying each other;
    an inner case sealed within said outer case, said inner case having a top and bottom, wherein at least a portion of said top and bottom have optically flat transparent surfaces parallel to and substantially overlying each other and parallel to and substantially between said optically flat transparent surfaces of said outer case;
    and means for mounting said intraocular lens within said inner case such that said intraocular lens lies in a plane parallel to and substantially between said optically flat transparent surfaces of said inner and outer cases.

2. The packaging system as claimed in claim 1, including:
    means for viewing said intraocular lens from the side of said packaging system.

3. The packaging system as claimed in claim 2, wherein said side viewing means includes:
    a transparent side window in the side of said outer case;
    and a transparent side window in the side of said inner case between said transparent side window in said side of said outer case and said intraocular lens.

4. The packaging system as claimed in claim 1, wherein:
    said optically flat transparent surfaces of said outer case includes top and bottom transparent windows substantially overlying each other, said top and bottom windows being optically flat and parallel to each other, and said top and bottom windows being recessed in the outer surface of said outer case.

5. The packaging system as claimed in claim 1, including:
    means for spacing said optically flat transparent surfaces of said inner case apart from said optically flat transparent surfaces of said outer case.

6. The packaging system as claimed in claim 1, wherein said mounting means includes:
    a tray inserted within said inner case;
    a post connected to said tray;

and means for attaching said intraocular lens to said post.

7. The packaging system as claimed in claim 6, wherein:
said tray includes a flat bottom having a view port therein;
and said post is positioned for mounting said intraocular lens over said view port.

8. The packaging system as claimed in claim 1, including:
means for sterilizing the interior of said packaging system.

9. The packaging system as claimed in claim 8, wherein said sterilizing means includes:
microporous gas permeable means for sealing said outer case such that a sterilizing agent may be introduced into and withdrawn from said outer case;
means for spacing said inner case apart from said outer case such that said sterilizing agent can substantially completely fill the space between said inner and outer cases;
and gas port means in said inner case for allowing said sterilizing agent to enter and exit the interior of said inner case to sterilize said intraocular lens.

10. An intraocular lens packaging system, which comprises:
a two-piece outer case, said outer case having a viewing portion and a cap portion, said viewing portion including a top window and a bottom window substantially overlying each other, said top and bottom windows each being optically flat and parallel to each other;
an inner case insertable within said outer case, said inner case having a bottom and a top, said top being movable between an open and a closed position, said top and bottom each having optically flat transparent surfaces, wherein said optically flat transparent surfaces are parallel to each other when said top is in said closed position;
a mounting tray insertable within said inner case, said mounting tray including a flat bottom portion adapted for overlying said bottom of said inner case parallel thereto, said flat bottom portion having a viewing port therein and a pair of mounting posts connected to said flat bottom portion and extending upwardly therefrom, said mounting posts being spaced circumferentially about said viewing port, and means for suspending said intraocular lens between said mounting posts over said viewing port such that said intraocular lens lies in a plane parallel to said flat bottom portion;
means for aligning said inner case within said outer case such that said top and bottom of said inner case are parallel to and between said top and bottom windows of said outer case;
and means for sealingly connecting said viewing portion and cap portion of said outer case with said inner case and mounting tray inserted therein.

11. The packaging system as claimed in claim 10, including:
a side window in said outer case adjacent to said intraocular lens;
and a side window in said inner case between said intraocular lens and said side window in said outer case.

12. The packaging system as claimed in claim 11, including:
an end window in said outer case adjacent to said intraocular lens;
and an end window in said inner case between said intraocular lens and said back window in said outer case.

13. The packaging system as claimed in claim 10, wherein:
said means for sealingly connecting said viewing portion and said cap portion of said outer case includes microporous gas permeable means for allowing a sterilizing agent to enter and exit said outer case, and said packaging system further includes:
means for spacing said inner case apart from said outer case to allow said sterilizing agent to fill substantially the entire space between said inner and outer cases;
and gas port means in said inner case for allowing said sterilizing agent to flow into and out of said inner case to sterilize said intraocular lens.

* * * * *